(12) United States Patent
Goldenberg et al.

(10) Patent No.: US 7,323,168 B2
(45) Date of Patent: Jan. 29, 2008

(54) IMMUNOTHERAPY FOR CHRONIC MYELOCYTIC LEUKEMIA

(75) Inventors: David M. Goldenberg, Mendham, NJ (US); Hans J. Hansen, Picayune, MS (US)

(73) Assignee: Immunomedics, Inc., Morris Plains, NJ (US)

( * ) Notice: Subject to any disclaimer, the term of this patent is extended or adjusted under 35 U.S.C. 154(b) by 60 days.

(21) Appl. No.: 10/853,150

(22) Filed: May 26, 2004

(65) Prior Publication Data

US 2004/0213796 A1 Oct. 28, 2004

Related U.S. Application Data

(62) Division of application No. 09/924,103, filed on Aug. 8, 2001, now Pat. No. 6,759,045.

(60) Provisional application No. 60/223,698, filed on Aug. 8, 2000.

(51) Int. Cl.
*A61K 39/395* (2006.01)
(52) U.S. Cl. .................................. 424/130.1
(58) Field of Classification Search ............... None
See application file for complete search history.

(56) References Cited

U.S. PATENT DOCUMENTS 4,904,596 A * 2/1990 Hakomori ................... 435/7.23

FOREIGN PATENT DOCUMENTS

CA 2279474 A1 1/2000

OTHER PUBLICATIONS

Jurcic et al (Clin. Cancer Res. Feb. 2000; 6:372-380).*
Kossman et al (Clin. Cancer Res. Oct. 1999;5:2748-2755).*
Jurcic et al (Leukemia Feb. 1995, 9(2);244-248).*
Warrell RP et al (Leukemia Jun. 1994;8(6):929-933).*
Shen et al (Blood May 1997; 89(9):3354-3360).*
Chen et al (Blood May 1997; 89(9):3345-3353).*
P. Caron et al., "Supersaturating Infusional Humanized Anti-CD33 Monoclonal Antibody HuM195 in Myelogenous Leukemia[1]," Clinical Cancer Research, Jun. 1998, pp. 1421-1428, vol. 4.
H. Hansen et al., "Characterization of Second-Generation Monoclonal Antibodies Against Carcinoembryonic Antigen", Cancer, Jun. 1993, pp. 3478-3485, vol. 71, No. 11.
J. Kotzerke et al., "Use of Re-188-Labeled Anti NCA-95 Antibodies in Treatment of Leukemia: First Results", Journal of Nuclear Medicine, May 1999, vol. 40, No. 5, Abstract.
R. Di Noto et al., "In Vitro Treatment of APL Cells with Arsenic Trioxide ($As_2O_3$) Results in a Highly Specific Induction of Solitary CD66c Display", Blood, Nov. 1997, vol. 90, No. 10, Abstract.
Seybold K. (Nuclear Medicine Communications, (1988) 9/10:745-752).

* cited by examiner

*Primary Examiner*—Christopher Yaen
(74) *Attorney, Agent, or Firm*—Faegre & Benson, LLP; Richard A. Nakashima

(57) ABSTRACT

Immunotherapy utilizing naked anti-granulocyte antibodies provides an effective means for treating chronic myelocytic leukemia (CML). Such antibodies can be administered alone or in combination with other therapies, such as immunoconjugates or chemotherapeutics. In either format, an effective therapy for treating CML is provided, which avoids the toxic side-effects typically associated with cancer therapy. The disclosed immunotherapy also is effective for treating acute myelocytic leukemia (AML) when co-administered with inducing agents which induce expression of antigens minimally displayed on the surface of myeloblasts.

6 Claims, No Drawings

IMMUNOTHERAPY FOR CHRONIC MYELOCYTIC LEUKEMIA

This application is a Divisional of U.S. patent application Ser. No. 09/924,103, filed Aug. 8, 2001 now U.S. Pat. No. 6,759,045, which claims benefit to U.S. Application No. 60/223,698, filed Aug. 8, 2000, the entire contents of the above-identified applications are hereby incorporated by reference.

BACKGROUND OF THE INVENTION

Chronic myelocytic leukemia (CML) is a highly specific disease that is defined by strict hematologic parameters that include a pathognomonic differential leukocyte count. Usually, CML is accompanied by the presence, in bone marrow cells, of the Ph chromosome, the first chromosomal anomaly to be regularly associated with a human neoplastic disease. Chronic myelocytic leukemia is a disease of worldwide distribution and predominantly appears during middle age. The disease is characterized by an initial chronic phase when it behaves as a differentiated neoplasm and responds very well to simple, nonintensive therapy. After a variable interval, CML metamorphosizes to a refractory phase that responds poorly or not at all to therapy, even when intensive. See Spiers, *Semin. Oncol.*, 22(4):380-95 (1995). At the stage of metamorphosis a great variety of clinical and hematologic pictures occur, and CML may mimic a myeloproliferative disease, a myelodysplasia, a subacute leukemia, acute myelocytic leukemia (AML), or acute lymphocytic leukemia (ALL). The old concept of an abrupt, explosive transition from the chronic phase to a so-called blastic crisis is incorrect. See Spiers, *Semin. Oncol.*, 22(4):380-95 (1995). In most cases, CML is observed to undergo two or more stepwise evolutions, e.g., from chronic phase to an accelerated myeloproliferative phase to a phase that resembles AML.

A variety of therapies have been used to treat CML. Traditional methods for treating leukemia, including chemotherapy and radiotherapy, have limited utility due to toxic side effects. The use of monoclonal antibodies to direct radionuclides, toxins or other therapeutic agents selectively to tumor sites has reduced the level of toxicity to normal tissues. However, due to the large quantities of conjugate which must be administered, such therapies continue to produce toxic side-effects. These aspects limit the effectiveness and duration of such treatments. Another therapy, allogeneic bone marrow transplants, has had the largest impact on survival among patients with CML. See Clarkson, *J. Clin. Oncol.*, 3:135-139 (1985). Like the previous therapies, however, bone marrow transplants are poorly tolerated by patients.

Recent studies suggest that immunotherapy utilizing naked antibodies can be an effective tool for treating certain cancers. The use of naked, humanized, anti-CD33 antibodies has proved effective in treating acute myelocytic leukemia and in reducing the residual disease in patients. See Caron et al., *Clin. Cancer Res.*, 4:1421-1428 (1998); Jurcic et al., *Clin. Cancer Res.*, 6:372-380 (2000). Similarly, immunotherapy comprising naked, humanized, anti-HER2/neu antibodies has produced promising results in the treatment of breast cancer. See Baselga et al., *Semin. Oncol.*, 26:78-83 (1999); Weiner, *Semin. Oncol.*, 26:43-51 (1999). Unconjugated immunoglobulins directed against CD20 have been shown to induce partial and complete responses in up to 50% of patients with advanced, indolent non-Hodgkin's lymphoma. See Weiner, *Semin. Oncol.*, 26:43-51 (1999).

The use of naked antibodies for treating malignancies has several advantages. First, immunotherapy comprising solely naked antibodies lacks the toxic side-effects associated with other therapies, such as radioimmunotherapy (RAIT) or immunotherapy utilizing conjugated toxins. Second, circulating naked antibodies remain therapeutically active longer than other therapies. For example, the effectiveness of RAIT is limited by the half-life of the conjugated isotope, typically a week or less. Similarly, the efficacy of conjugated immunotoxins can be short-lived due to in vivo modification of the toxin. Third, since naked antibodies are well-tolerated by patients, multiple rounds of therapy can be administered. Fourth, combination therapy utilizing naked antibodies is better tolerated by patients because lower quantities of the toxic component of the combination are required to achieve effective results. Finally, the use of naked antibodies dramatically reduces the costs of treating cancer by reducing the need for expensive radioactive or therapeutic conjugates which possess short shelf-lives and whose administration typically requires special facilities and personnel. Thus, such cost reductions enable more patients to benefit from the therapy.

There is a need, therefore, to develop immunotherapies which utilize naked antibodies to treat CML. Such therapies would cost-effectively treat patients without inducing toxic side-effects

SUMMARY OF THE INVENTION

Accordingly, it is one object of the present invention to provide methods of treating myelocytic leukemia using naked immunotherapy.

In accomplishing this and other objects, there is provided, in accordance with one aspect of the present invention, a method for treating chronic myelocytic leukemia (CML) in a patient, comprising administering to the patient a therapeutic composition comprising a pharmaceutically acceptable carrier and at least one naked anti-granulocyte antibody. A variety of anti-granulocyte antibodies can be used in the present invention. Examples include, but are not limited to, anti-NCA-90, anti-NCA-95, MN-2, MN-15, NP-1 and NP-2. In one embodiment, a single, naked anti-granulocyte antibody is administered to a patient while, in another, more than one anti-granulocyte antibody is administered. In still another embodiment, at least one naked anti-granulocyte antibody is administered to a patient in combination with naked antibodies directed to antigens present on a single granulocyte precursor, such as anti-CD33 or anti-CD15 antibodies.

In another embodiment of the present invention, naked anti-granulocyte antibodies are used in combination with other cancer therapies, e.g., an immunoconjugate or chemotherapy. Preferred immunoconjugates include radiolabeled antibody components and conjugates of an anti-granulocyte antibody component and an immunomodulator, such as a cytokine, stem cell growth factor, lymphotoxin or hematopoietic factor. In still another embodiment, combination therapy of the present invention can comprise antibody-toxin fusion proteins.

In yet another embodiment of the present invention, naked anti-granulocyte antibodies are administered in combination with inducing agents which either enhance or induce the expression of the targeted antigen. Such inducing agents enhance the efficacy of the administered therapy by up-regulating the expression of the target antigen on the surface of a cell of interest. In addition, inducing agents can extend the inventive therapy's tumor-killing potential to additional cell-types and cancers by inducing expression of antigens not normally displayed on the surface of these cells. Accordingly, the antibodies of the present invention can be used to treat AML, as well as CML.

Thus, in another embodiment of the present invention, there is provided a method for treating acute myelocytic leukemia (AML) or acute promyelocytic leukemia (APML) in a patient, comprising administering to the patient a therapeutic composition comprising a pharmaceutically acceptable carrier and at least one naked anti-granulocyte antibody and an inducing agent, wherein the inducing agent induces expression of antigens which are minimally displayed on the surface of myeloblasts. As described above, the inventive method can be further combined with other naked, anti-granulocyte antibodies, antibody-toxin fusion proteins and other cancer therapies, e.g., an immunoconjugate or chemotherapy.

Other objects, features and advantages of the present invention will become apparent from the following detailed description. The detailed description and specific examples, while indicating preferred embodiments, are given for illustration only since various changes and modifications within the spirit and scope of the invention will become apparent to those skilled in the art from this detailed description. Further, the examples demonstrate the principle of the invention and cannot be expected to specifically illustrate the application of this invention to all the examples of infections where it obviously will be useful to those skilled in the prior art.

DETAILED DESCRIPTION

The present invention provides improved methods for treating myelocytic leukemia, particularly CML. The inventive methods utilize naked granulocyte-specific antibodies to destroy myeloid leukemia cells without the toxic side-effects normally associated with previous forms of therapy. In one embodiment, the treatment utilizes only naked granulocyte-specific antibodies. In another embodiment, the naked antibodies are used in combination with immunoconjugates or other therapeutics. In either form of therapy, the patient is provided an effective treatment for chronic myelocytic leukemia that avoids the toxic side-effects that accompany administration of typical amounts of anti-cancer medicaments.

The anti-granulocyte antibodies used in the present invention are directed to antigens associated with various cell-types in the granulocyte lineage. Unlike in AML, malignant myeloblasts of CML patients differentiate into a variety of cell-types, including myelocytes, metamyelocytes, bands, and granulocytes. Accordingly, immunotherapy directed to one or two of these cell-types is incapable of meaningfully reducing the number of leukemic cells. Since the antibodies of the inventive therapy recognize immature and mature granulocytes, the present invention provides an effective method for ridding malignant cells from a CML patient's bone marrow.

A variety of anti-granulocyte antibodies can be used in the present invention. In one embodiment, the inventive methods utilize anti-NCA-90 antibodies. A preferred example of such an antibody is MN-3. See Hansen et al., *Cancer*, 71:3478-3485 (1993); Becker et al., *Semin. Nucl. Med.*, 24(2):142-53 (1994). In another embodiment, anti-NCA-95 antibodies are used. In still other embodiments, MN-2 and NP-2, which are class IIa anti-CEA antibodies, and MN-15 and NP-1, which are class I anti-CEA antibodies, are utilized. See Hansen et al., *Cancer*, 71:3478-3485 (1993); Primus et al., *Cancer Res.*, 43:686-692 (1983). Human and chimeric forms of these antibodies are preferred, and full-human and humanized versions are most preferred.

Definitions

In the description that follows, a number of terms are used extensively. The following definitions are provided to facilitate understanding of the invention.

The term "myelocytic leukemia" is synonymous with the terms granulocytic leukemia, myelogenic leukemia, myelogenous leukemia and myeloid leukemia.

Chronic myelocytic leukemia is characterized by an uncontrolled proliferation of myelopoietic cells in the bone marrow and extramedullary sites in which the malignant myeloblast is able to differentiate and give rise to myelocytes, metamyelocytes, band cells and granulocytes.

Acute myelocytic leukemia is characterized by an uncontrolled proliferation of myeloblasts which are unable to differentiate into more mature cell-types.

The term "anti-granulocyte antibody" refers to an antibody which recognizes an antigen which is present on two or more cell-types of the granulocyte/myelocyte lineage.

A "chimeric antibody" is a recombinant protein that contains the variable domains and complementary determining regions derived from a rodent antibody, while the remainder of the antibody molecule is derived from a human antibody.

"Humanized antibodies" are recombinant proteins in which murine complementarity determining regions of a monoclonal antibody have been transferred from heavy and light variable chains of a murine immunoglobulin into a human variable domain.

A "therapeutic agent" is a molecule or atom which may be conjugated to an antibody moiety to produce a conjugate, which is useful for therapy. Examples of therapeutic agents include, but are not limited to, drugs, toxins, immunomodulators, boron compounds, photoactive agents or dyes, cytokines, hormones radiopharmaceuticals and radioisotopes.

A "naked antibody" is an entire antibody, as opposed to an antibody fragment, which is not conjugated to a therapeutic agent. Naked antibodies include both polyclonal and monoclonal antibodies, as well as certain recombinant antibodies, such as chimeric and humanized antibodies.

The term "antibody component" includes both an entire antibody and an antibody fragment.

An "immunoconjugate" is a conjugate of an antibody component with a therapeutic agent.

The term "antibody fusion protein" refers to a recombinant molecule that comprises one or more antibody components and a therapeutic agent. Examples of therapeutic agents suitable for such fusion proteins include immunomodulators ("antibody-immunomodulator fusion protein") and toxins ("antibody-toxin fusion protein"). The fusion protein may comprise a single antibody component, a multivalent combination of different antibody components or multiple copies of the same antibody component.

A "structural gene" is a DNA sequence that is transcribed into messenger RNA (mRNA) which is then translated into a sequence of amino acids characteristic of a specific polypeptide.

A "promoter" is a DNA sequence that directs the transcription of a structural gene. Typically, a promoter is located in the 5' region of a gene, proximal to the transcriptional start site of a structural gene. If a promoter is an inducible promoter, then the rate of transcription increases in response to an inducing agent. In contrast, the rate of transcription is not regulated by an inducing agent if the promoter is a constitutive promoter.

An "isolated DNA molecule" is a fragment of DNA that is not integrated in the genomic DNA of an organism. For example, a cloned antibody gene is a DNA fragment that has been separated from the genomic DNA of a mammalian cell. Another example of an isolated DNA molecule is a chemically-synthesized DNA molecule that is not integrated in the genomic DNA of an organism.

An "enhancer" is a DNA regulatory element that can increase the efficiency of transcription, regardless of the distance or orientation of the enhancer relative to the start site of transcription.

"Complementary DNA" (cDNA) is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand.

The term "expression" refers to the biosynthesis of a gene product. For example, in the case of a structural gene, expression involves transcription of the structural gene into mRNA and the translation of mRNA into one or more polypeptides.

A "cloning vector" is a DNA molecule, such as a plasmid, cosmid or bacteriophage, that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance.

An "expression vector" is a DNA molecule comprising a gene that is expressed in a host cell. Typically, gene expression is placed under the control of certain regulatory elements, including constitutive or inducible promoters, tissue-specific regulatory elements, and enhancers. Such a gene is said to be "operably linked to" the regulatory elements.

A "recombinant host" may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

An "antibody fragment" is a portion of an antibody such as $F(ab')_2$, $F(ab)_2$, Fab', Fab, and the like. Regardless of structure, an antibody fragment binds with the same antigen that is recognized by the intact antibody. For example, an anti-CD22 monoclonal antibody fragment binds with an epitope of CD22.

The term "antibody fragment" also includes any synthetic or genetically engineered protein that acts like an antibody by binding to a specific antigen to form a complex. For example, antibody fragments include isolated fragments consisting of the light chain variable region, "Fv" fragments consisting of the variable regions of the heavy and light chains, recombinant single chain polypeptide molecules in which light and heavy variable regions are connected by a peptide linker ("sFv proteins"), and minimal recognition units consisting of the amino acid residues that mimic the hypervariable region.

Production of Antibodies

Rodent monoclonal antibodies specific for granulocytes can be obtained by methods known to those skilled in the art. See generally Kohler and Milstein, *Nature* 256:495 (1975); Coligan et al. (eds.), CURRENT PROTOCOLS IN IMMUNOLOGY (John Wiley & Sons 1991). Briefly, monoclonal antibodies can be obtained by injecting mice with a composition comprising, for example, NCA-90, verifying the presence of antibody production by removing a serum sample, removing the spleen to obtain B-lymphocytes, fusing the B-lymphocytes with myeloma cells to produce hybridomas, cloning the hybridomas, selecting positive clones which produce anti-NCA-90 antibodies, culturing the clones that produce antibodies to the antigen and isolating the antibodies from the hybridoma cultures.

Monoclonal antibodies can be isolated and purified from hybridoma cultures by a variety of well-known techniques. Such isolation techniques include affinity chromatography with Protein-A Sepharose, size-exclusion chromatography, and ion-exchange chromatography. See Coligan et al. (eds.), CURRENT PROTOCOLS IN IMMUNOLOGY (John Wiley & Sons 1991); Baines et al., pages 79-104, METHODS IN MOLECULAR BIOLOGY (The Humana Press, Inc. 1992).

Suitable amounts of the NCA-90 antigen, also referred to as CD66c, can be obtained using standard techniques well-known in the art. For example, NCA-90 protein can be obtained from transfected cultured cells that overproduce NCA-90. Expression vectors that comprise DNA molecules encoding NCA-90 can be constructed using the published NCA-90 nucleotide sequence. See Oikawa et al., *Biochem. Biophys. Res. Commun.*, 146:464-460 (1987); Wilson et al., *J. Exp. Med.* 173:137 (1991); Wilson et al., *J. Immunol.* 150:5013 (1993). Similarly, expression vectors for producing NCA-95 protein can be constructed using the published NCA-95 nucleotide sequence. See Berling et al., *Cancer Res.*, 50:6534-6539 (1990).

As an illustration, DNA molecules encoding NCA-90 can be obtained by synthesizing DNA molecules using mutually priming long oligonucleotides. See Ausubel et al., (eds.), CURRENT PROTOCOLS IN MOLECULAR BIOLOGY (John Wiley & Sons, Inc. 1990); Wosnick et al., *Gene* 60:115 (1987); Ausubel et al. (eds.), SHORT PROTOCOLS IN MOLECULAR BIOLOGY (John Wiley & Sons, Inc. 1995). Established techniques using the polymerase chain reaction provide the ability to synthesize genes as large as 1.8 kilobases in length. Adang et al., *Plant Molec. Biol.*, 21:1131 (1993); Bambot et al., *PCR Methods and Applications*, 2:266 (1993); White (ed.), METHODS IN MOLECULAR BIOLOGY, pages 263-268 (Humana Press, Inc. 1993). In a variation of this approach, an anti-NCA-90 monoclonal antibody can be obtained by fusing myeloma cells with spleen cells from mice immunized with a murine pre-B cell line stably transfected with NCA-90 cDNA using techniques well-known in the art.

One example of a suitable murine anti-NCA-90 monoclonal antibody is the MN-3 monoclonal antibody. The MN-3 antibody was isolated from hybridomas derived from BALB/c mice which were immunized with partially purified carcinoembryonic antigen (CEA) derived from GW-39 human colon adenocarcinoma xenografts. See Hansen et al., *Cancer*, 71:3478-3485 (1993). The MN-3 antibody is specific for the NCA-90 antigen, a homotypic adhesion molecule expressed on granulocytes, as well as normal colonic mucosa and colonic adenocarcinoma. See Becker et al., *Semin. Nucl. Med.*, 24(2):142-53 (1994); Watt et. al., *Blood*, 78:63-74 (1991).

One example of a suitable murine anti-NCA-95 antibody is the BW 250/183 antibody. See Bosslet et al., *Int. J. Cancer,* 36:75-84 (1985); Meller et al., *J. Nucl. Med.,* 39:1248-1253. Another useful anti-NCA-95 antibody is Mab 47. See Audette et al., *Mol. Immunol.,* 24:1177-1186 (1987).

Another suitable antibody is the MN-2 monoclonal antibody. The MN-2 antibody was isolated from hybridomas derived from BALB/c mice which were immunized with partially purified carcinoembryonic antigen (CEA) derived from GW-39 human colon adenocarcinoma xenografts. See Hansen et al., *Cancer,* 71:3478-3485 (1993). As a class IIA anti-CEA antibody, MN-2 can be identified readily using blocking assays well-known in the art. See U.S. Pat. No. 4,818,709, which is hereby incorporated by reference in its entirety.

Another suitable antibody is the MN-15 monoclonal antibody. The MN-15 antibody displays cross-reactivity between NCA-90 and NCA-95. MN-15 was isolated from hybridomas derived from BALB/c mice which were immunized with partially purified carcinoembryonic antigen (CEA) derived from GW-39 human colon adenocarcinoma xenografts. See Hansen et al., *Cancer,* 71:3478-3485 (1993). As a class I anti-CEA antibody, MN-15 can be identified readily using blocking assays well-known in the art.

Still another suitable antibody is the NP-2 monoclonal antibody. The NP-2 has specificity similar to that of MN-2. NP-2 was isolated from hybridomas derived from BALB/c mice which were immunized with partially purified carcinoembryonic antigen (CEA) derived from liver metastases of human colonic adenocarcinoma according to the procedure of Krupey et al. (*Immunochem.,* 9: 617 (1972)), as modified by Newman et al. (*Cancer Res.,* 34:2125 (1974)). See Primus et al., *Cancer Res.,* 43:686-92 (1983); U.S. Pat. No. 4,818,709.

Yet another suitable antibody is the NP-1 monoclonal antibody. The NP-1 has similar specificity to that of MN-15. NP-1 was isolated from hybridomas derived from BALB/c mice which were immunized with partially purified carcinoembryonic antigen (CEA) derived from liver metastases of human colonic adenocarcinoma according to the procedure of Krupey et al. (*Immunochem.,* 9:617 (1972)), as modified by Newman et al. (*Cancer Res.,* 34:2125 (1974)). See Primus et al., *Cancer Res.,* 43:686-92 (1983); U.S. Pat. No. 4,818,709.

One example of an antibody suitable for multimodal therapy is M195. See U.S. Pat. No. 6,007,814. This antibody is specific for the CD33 antigen, which is present on myeloid cells and monocytic cells. M195 was produced from hybridomas resulting from a fusion of SP2/0-Ag14 mouse myeloma cells and the spleen cells of a 5-week-old BALB/c mouse immunized with leukemia cells from a patient with AML (FAB-M2).

Other examples of antibodies suitable for multimodal therapy are anti-SSEA-1 and PM-81. See Thakur et al., *J. Nucl. Med.,* 37:1789-1795 (1996); Ball et al., *J. Immunol.,* 30:2937-2941(1983). These antibodies recognize CD-15 antigens, which are present on a variety of myeloid cells. Anti-SSEA-1 is produced from a hybridoma derived from mouse teratocarcinoma cells. PM-81 is produced from a hybridoma derived from a fusion of cells of the NS-1 myeloma cell line with cells from a mouse immunized with the HL-60 promyelocytic leukemia cell line.

In an additional embodiment, an antibody of the present invention is a chimeric antibody in which the variable regions of a human antibody have been replaced by the variable regions of a, e.g., rodent anti-NCA-90 antibody. The advantages of chimeric antibodies include decreased immunogenicity and increased in vivo stability. Techniques for constructing chimeric antibodies are well-known to those of skill in the art. See Leung et al., *Hybridoma,* 13:469 (1994).

In another embodiment, an antibody of the present invention is a subhuman primate antibody. General techniques for raising therapeutically useful antibodies in baboons may be found, for example, in Goldenberg et al., International Patent Publication No. WO 91/11465 (1991), which is hereby incorporated by reference in its entirety, and in Losman et al., *Int. J. Cancer,* 46:310 (1990).

In yet another embodiment, an antibody of the present invention is a "humanized" monoclonal antibody. That is, mouse complementarity determining regions are transferred from heavy and light variable chains of the mouse immunoglobulin into a human variable domain, followed by the replacement of some human residues in the framework regions of their murine counterparts. Humanized monoclonal antibodies in accordance with this invention are suitable for use in therapeutic methods. General techniques for cloning murine immunoglobulin variable domains are described, for example, by the publication of Orlandi et al., *Proc. Nat'l Acad. Sci. USA,* 86:3833 (1989). Techniques for producing humanized monoclonal antibodies are described, for example, by Jones et al., *Nature,* 321:522 (1986), Riechmann et al., *Nature,* 332:323 (1988), Verhoeyen et al., *Science,* 239:1534 (1988), Carter et al., *Proc. Nat'l Acad. Sci. USA,* 89:4285 (1992), Sandhu, *Crit. Rev. Biotech.,* 12:437 (1992) and Singer et al., *J. Immun.,* 150:2844 (1993).

In another embodiment, an antibody of the present invention is a human monoclonal antibody. Such antibodies are obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are well-known in the art. See Green et al., *Nature Genet.,* 7:13 (1994); Lonberg et al., *Nature,* 368:856 (1994); Taylor et al., *Int. Immun.,* 6:579 (1994); Bruggeman et al., *Curr. Opin. Biotechnol.,* 8:455-458 (1997). Alternatively, human antibodies to antigens of interest also can be obtained using phage display. See Aujame et al., *Hum. Antibodies,* 8:155-168 (1997).

Preparation of Immunoconjugates

The present invention contemplates the use of naked anti-granulocyte antibodies as the primary therapeutic composition of CML. However, in one embodiment of the invention, naked anti-granulocyte antibodies, e.g., MN-3 or MN-2, are administered to a patient in combination with one or more immunoconjugates. Such immunoconjugates can be prepared by conjugating a therapeutic agent to an antibody component. General techniques are described in Shih et al., *Int. J. Cancer,* 41:832-839 (1988), Shih et al., *Int. J. Cancer,* 46:1101-1106 (1990) and U.S. Pat. No. 5,057,313, which are hereby incorporated by reference in their entireties. The general method involves reacting an antibody component having an oxidized carbohydrate portion with a carrier polymer that has at least one free amine function and that is loaded with a plurality of drug., toxin, chelator, boron addends or other therapeutic agents. This reaction results in an initial Schiff base (imine) linkage, which can be stabilized by reduction to a secondary amine to form the final conjugate.

The carrier polymer is preferably an aminodextran or polypeptide of at least 50 amino acid residues, although other substantially equivalent polymer carriers also can be used. For ease of administration and effective targeting, the final immunoconjugate is preferably soluble in an aqueous solution, such as mammalian serum. Thus, solubilizing functions on the carrier polymer will enhance the serum solubility of the final immunoconjugate. In particular, an aminodextran is preferred.

The process for preparing an immunoconjugate with an aminodextran carrier typically begins with a dextran polymer, advantageously a dextran of average molecular weight of about 5,000-100,000. The dextran is reacted with an oxidizing agent to effect a controlled oxidation of a portion of its carbohydrate rings to generate aldehyde groups. The oxidation is conveniently effected with glycolytic chemical reagents such as $NaIO_4$, according to conventional procedures.

The oxidized dextran is then reacted with a polyamine, preferably a diamine, and more preferably, a mono- or polyhydroxy diamine. Suitable amines include ethylene diamine, propylene diamine or other like polymethylene diamines, diethylene triamine or like polyamines, 1,3-diamino-2-hydroxypropane or other like hydroxylated diamines or polyamines and the like. An excess of the amine relative to the aldehyde groups of the dextran is used to ensure substantially complete conversion of the aldehyde functions to Schiff base groups.

A reducing agent, such as $NABH_4$, $NaBH_3CN$ or the like, is used to effect reductive stabilization of the resultant Schiff base intermediate. The resultant adduct can be purified by passage through a conventional sizing column to remove cross-linked dextrans. Other conventional methods of derivatizing a dextran to introduce amine functions also can be used, e.g., reaction with cyanogen bromide, followed by reaction with a diamine. The aminodextran then is reacted with a derivative of the particular drug, toxin, chelator, immunomodulator, boron addend or other therapeutic agent to be loaded, in an activated form, preferably, a carboxyl-activated derivative, prepared by conventional means, e.g., using dicyclohexylcarbodiimide (DCC) or a water-soluble variant thereof, to form an intermediate adduct.

Alternatively, polypeptide toxins such as pokeweed antiviral protein or ricin A-chain and the like, can be coupled to aminodextran by glutaraldehyde condensation or by reaction of activated carboxyl groups on the protein with amines on the aminodextran. Chelators for radiometals or magnetic resonance enhancers are well-known in the art. Typical are derivatives of ethylenediaminetetraacetic acid (EDTA), diethylene-triaminepentaacetic acid (DTPA) and 1,4,7,10-tetraazacyclododecane-N,N',N'',N'''-tetraacetic acid (DOTA). These chelators typically have groups on the side chain by which the chelator can be attached to a carrier. Such groups include, e.g., benzylisothiocyanate, by which the DTPA or EDTA can be coupled to the amine group of a carrier. Alternatively, carboxyl groups or amine groups on a chelator can be coupled to a carrier by activation or prior derivatization and then coupling, all by well-known means.

Boron addends, such as carboranes, can be attached to antibody components by conventional methods. For example, carboranes can be prepared with carboxyl functions on pendant side chains, as is well-known in the art. Attachment of such carboranes to a carrier, e.g., aminodextran, can be achieved by activation of the carboxyl groups of the carboranes and condensation with amines on the carrier to produce an intermediate conjugate. Such intermediate conjugates then are attached to antibody components to produce therapeutically useful immunoconjugates, as described below.

A polypeptide carrier can be used instead of aminodextran, but the polypeptide carrier must have at least 50 amino acid residues in the chain, preferably 100-5000 amino acid residues. At least some of the amino acids should be lysine residues or glutamate or aspartate residues. The pendant amines of lysine residues and pendant carboxylates of glutamine and aspartate are convenient for attaching a drug, toxin, immunomodulator, chelator, boron addend or other therapeutic agent. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier and immunoconjugate.

Conjugation of the intermediate conjugate with the antibody component is effected by oxidizing the carbohydrate portion of the antibody component and reacting the resulting aldehyde (and ketone) carbonyls with amine groups remaining on the carrier after loading with a drug, toxin, chelator, immunomodulator, boron addend or other therapeutic agent. Alternatively, an intermediate conjugate can be attached to an oxidized antibody component via amine groups that have been introduced in the intermediate conjugate after loading with the therapeutic agent. Oxidation is conveniently effected either chemically, e.g., with $NaIO_4$ or other glycolytic reagent, or enzymatically, e.g., with neuraminidase and galactose oxidase. In the case of an aminodextran carrier, not all of the amines of the aminodextran typically are used for loading a therapeutic agent. The remaining amines of aminodextran condense with the oxidized antibody component to form Schiff base adducts, which are then reductively stabilized, normally with a borohydride reducing agent.

Analogous procedures are used to produce other immunoconjugates according to the invention. Loaded polypeptide carriers preferably have free lysine residues remaining for condensation with the oxidized carbohydrate portion of an antibody component. Carboxyls on the polypeptide carrier can be converted, if necessary, to amines by, e.g., activation with DCC and reaction with an excess of a diamine. The final immunoconjugate is purified using conventional techniques, such as sizing chromatography on Sephacryl S-300.

Alternatively, immunoconjugates can be prepared by directly conjugating an antibody component with a therapeutic agent. The general procedure is analogous to the indirect method of conjugation except that a therapeutic agent is directly attached to an oxidized antibody component.

It will be appreciated that other therapeutic agents can be substituted for the chelators described herein. Those of skill in the art will be able to devise conjugation schemes without undue experimentation.

As a further illustration, a therapeutic agent can be attached at the hinge region of a reduced antibody component via disulfide bond formation. For example, the tetanus toxoid peptides can be constructed with a single cysteine residue that is used to attach the peptide to an antibody component. As an alternative, such peptides can be attached to the antibody component using a heterobifunctional cross-linker, such as N-succinyl 3-(2-pyridyldithio)proprionate (SPDP). See Yu et al., *Int. J. Cancer*, 56:244 (1994). General techniques for such conjugations are well-known in the art.

See Wong, CHEMISTRY OF PROTEIN CONJUGATION AND CROSS-LINKING (CRC Press 1991); Birch et al. (eds.), MONOCLONAL ANTIBODIES: PRINCIPLES AND APPLICATIONS, pages 187-230 (Wiley-Liss, Inc. 1995); Ritter et al. (eds.), MONOCLONAL ANTIBODIES: PRODUCTION, ENGINEERING AND CLINICAL APPLICATION, pages 60-84 (Cambridge University Press 1995).

As described above, carbohydrate moieties in the Fc region of an antibody can be used to conjugate a therapeutic agent. However, the Fc region is absent if an antibody fragment is used as the antibody component of the immunoconjugate. Nevertheless, it is possible to introduce a carbohydrate moiety into the light chain variable region of an antibody or antibody fragment. See Leung et al., J. Immunol., 154:5919 (1995); U.S. Pat. No. 5,443,953, which are hereby incorporated by reference in their entireties. The engineered carbohydrate moiety then is used to attach a therapeutic agent.

In addition, those of skill in the art will recognize numerous possible variations of the conjugation methods. For example, the carbohydrate moiety can be used to attach polyethyleneglycol in order to extend the half-life of an intact antibody, or antigen-binding fragment thereof, in blood, lymph or other extracellular fluids. Moreover, it is possible to construct a "divalent immunoconjugate" by attaching therapeutic agents to a carbohydrate moiety and to a free sulfhydryl group. Such a free sulfhydryl group may be located in the hinge region of the antibody component.

Production of Antibody Fragments

Immunocongugates utilized in combination therapies of the present invention can comprise antibody fragments. Such antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent and, optionally, a blocking group for the sulfhydryl groups resulting from cleavage of disulfide linkages, to produce 3.5S Fab' monovalent fragments. Alternatively, an enzymatic cleavage using pepsin produces two monovalent Fab fragments and an Fc fragment directly. These methods are described, for example, in U.S. Pat. Nos. 4,036,945 and 4,331,647 and the references contained therein. See also Nisonoff et al., Arch. Biochem. Biophys., 89:230 (1960); Porter, Biochem. J., 73:119 (1959); Edelman et al., METHODS IN ENZYMOLOGY, page 422 (Academic Press 1967), and Coligan et al. (eds.), CURRENT PROTOCOLS IN IMMUNOLOGY, (John Wiley & Sons 1991).

Other methods of cleaving antibodies, such as separation of heavy chains to form monovalent light-heavy chain fragments, further cleavage of fragments or other enzymatic, chemical or genetic techniques also may be used, so long as the fragments bind to the antigen that is recognized by the intact antibody. For example, Fv fragments comprise an association of $V_H$ and $V_L$ chains. This association can be noncovalent, as described in Inbar et al., Proc. Nat'l. Acad. Sci. USA, 69:2659 (1972). Alternatively, the variable chains can be linked by an intermolecular disulfide bond or crosslinked by chemicals such as glutaraldehyde. See Sandhu, Crit. Rev. Biotech., 12:437 (1992).

Preferably, the Fv fragments comprise $V_H$ and $V_L$ chains which are connected by a peptide linker. These single-chain antigen binding proteins (sFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as E. coli. The recombinant host cells synthesize a single polypeptide chain with a linker peptide bridging the two V domains. Methods for producing sFvs are well-known in the art. See Whitlow et al., Methods: A Companion to Methods in Enymology 2:97 (1991); Bird et al., Science, 242:423 (1988); U.S. Pat. No. 4,946,778; Pack et al., Bio/Technology, 11:1271 (1993), and Sandhu, Crit. Rev. Biotech., 12:437 (1992).

Another form of an antibody fragment is a peptide coding for a single complementarity-determining region (CDR). CDR peptides ("minimal recognition units") can be obtained by constructing genes encoding the CDR of an antibody of interest Such genes are prepared, for example, by using the polymerase chain reaction to synthesize the variable region from RNA of antibody-producing cells. See Larrick et al., Methods: A Companion to Methods in Enzymology 2:106 (1991); Ritter et al. (eds.), MONOCLONAL ANTIBODIES: PRODUCTION, ENGINEERING AND CLINICAL APPLICATION, pages 166-179 (Cambridge University Press 1995); Birch et al., (eds.), MONOCLONAL ANTIBODIES: PRINCIPLES AND APPLICATIONS, pages 137-185 (Wiley-Liss, Inc. 1995).

Therapeutic Use of Anti-Granulocyte Antibodies

Since the antibodies of the inventive therapy recognize antigens present on immature and mature granulocytes, the present invention provides an effective method for ridding malignant cells from a patient with myelocytic leukemia, in particular CML. As discussed above, a variety of anti-granulocyte antibodies can be used in the inventive therapy.

The present invention contemplates the use of naked anti-granulocyte antibodies as the primary therapeutic composition for treatment of CML. Such a composition can contain polyclonal anti-granulocyte antibodies or monoclonal anti-granulocyte antibodies.

Methods for determining the binding specificity of an anti-granulocyte antibody are well-known to those of skill in the art. General methods are provided, for example, by Manson (ed.), METHODS IN MOLECULAR BIOLOGY: IMMUNOCHEMICAL PROTOCOLS, pages 105-116 (The Humana Press, Inc. 1992). The epitope specificity also can be identified by binding a test antibody with a panel of antigens which lack particular domains.

In another embodiment of the present invention, naked anti-granulocyte antibodies can be used in combination with other cancer therapies, e.g., an immunoconjugate or chemotherapy. Such combination regimens are advantageous over therapies previously practiced in the art because they achieve effective results with less toxins. Thus, such therapies eliminate or greatly reduce the negative side-effects typically associated with cancer therapy. In such multimodal regimens, the supplemental therapeutic compositions can be administered before; concurrently, or after administration of the naked anti-granulocyte antibodies.

Preferred immunoconjugates include radiolabeled antibody components and conjugates of an anti-granulocyte antibody component and an immunomodulator. A radiolabeled immunoconjugate may comprise an α-emitting radioisotope, a β-emitting radioisotope, a γ-emitting radioisotope, an Auger electron emitter, a neutron capturing agent that emits α-particles or a radioisotope that decays by electron capture. Suitable radioisotopes include $^{198}$Au, $^{32}$P, $^{125}$I, $^{131}$I, $^{90}$Y, $^{186}$Re, $^{188}$Re, $^{67}$Cu, $^{211}$At, $^{213}$Bi, $^{224}$Ac, and the like. Boron addends are preferred neutron capture agents that are converted to alpha-emitters.

As discussed above, a radioisotope can be attached to an antibody component directly or indirectly, via a chelating agent. For example, $^{67}$Cu, considered one of the more promising radioisotopes for radioimmunotherapy due to its 61.5 hour half-life and abundant supply of beta particles and gamma rays, can be conjugated to an antibody component using the chelating agent, p-bromoacetamido-benzyl-tetra-ethylaminetetraacetic acid (TETA). See Gennaro et al. (eds.), REMINGTON'S PHARMACEUTICAL SCIENCES, pages 624-652 (Mack Publishing Co. 1990). Alternatively, $^{90}$Y, which emits an energetic beta particle, can be coupled to an antibody component using DTPA or DOTA. Moreover, a method for the direct radiolabeling of the antibody component with $^{131}$I is described by Stein et al., *Antibody Immunoconj. Radiopharm.*, 4:703 (1991). Alternatively, boron addends such as carboranes can be attached to antibody components, as discussed above.

In another embodiment, immunoconjugates can comprise an immunomodulator moiety. As used herein, the term "immunomodulator" includes cytokines, stem cell growth factors, lymphotoxins, such as tumor necrosis factor (TNF), and hematopoietic factors, such as interleukins (e.g., interleukin-1 (IL-1), IL-2, IL-3, IL-6, IL-10 and IL-12), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S1 factor," erythropoietin and thrombopoietin. Examples of suitable immunomodulator moieties include IL-2, IL-6, IL-10, IL-12, interferon-γ, TNF-α and the like.

A related immunoconjugate is a fusion protein comprising one or more antibody moieties and an immunomodulator moiety. Useful antibody moieties include antibody components that bind with, for example, NCA-90 or NCA-95. Bivalent, trivalent and tetravalent constructs can be used in accordance with the invention.

Methods of making antibody-immunomodulator fusion proteins are well-known in the art. For example, antibody fusion proteins comprising an interleukin-2 moiety are described by Boleti et al., *Ann. Oncol.*, 6:945 (1995), Nicolet et al., *Cancer Gene Ther.*, 2:161 (1995), Becker et al., *Proc. Nat'l. Acad. Sci. USA*, 93:7826 (1996), Hank et al., *Clin. Cancer Res.*, 2:1951 (1996) and Hu et al., *Cancer Res.*, 56:4998 (1996). In addition, Yang et al. describe a fusion protein that includes an F(ab')$_2$ fragment and a tumor necrosis factor alpha moiety. See Yang et al., *Hum. Antibodies Hybridomas* 6:129 (1995).

Such immunoconjugates and antibody-immunomodulator fusion proteins provide a means to deliver an immunomodulator to a target cell and are particularly useful against tumor cells. The cytotoxic effects of immunomodulators are well-known in the art. See Pessuto et al. (eds.), BIOTECHNOLOGY AND PHARMACY, pages 53-70 (Chapman & Hall 1993). As an illustration, interferons can inhibit cell proliferation by inducing increased expression of class I histocompatibility antigens on the surface of various cells and, thus, enhance the rate of destruction of cells by cytotoxic T lymphocytes. Furthermore, tumor necrosis factors, such as TNF-α, are believed to produce cytotoxic effects by inducing DNA fragmentation.

Therapeutically useful immunoconjugates can be prepared in which an antibody component is conjugated to a toxin or a chemotherapeutic drug. Illustrative of toxins and drugs which are suitably employed in the preparation of such conjugates are calicheamicin, ricin, abrin, ribonuclease, DNase I, RNase, Staphylococcal enterotoxin-A, pokeweed antiviral protein, gelonin, diphtherin toxin, Pseudomonas exotoxin, and Pseudomonas endotoxin. See Pastan et al., *Cell*, 47:641 (1986),; Goldenberg, *CA, A Cancer Journal for Clinicians*, 44:43 (1994). For instance, one example of an effective immunoconjugate is an anti-NCA-90 antibody conjugated to RNase. Another example is an anti-CD33 antibody conjugated to calicheamicin. Other suitable toxins are well-known in the art, such as protein inhibitors, DNA, RNA and cell-cycle poisons.

In another embodiment, combination therapy utilizing naked, anti-granulocyte antibodies can comprise antibody-toxin fusion proteins. An antibody-toxin fusion protein is a fusion protein that comprises one or more antibody moieties and a toxin moiety. Useful antibody moieties include antibody components that bind with NCA-90 or NCA-95. Bivalent, trivalent and tetravalent constructs can be used in accordance with the invention. Methods for making antibody-toxin fusion proteins are well-known in the art. For example, antibody-*Pseudomonas* exotoxin A fusion proteins have been described by Chaudhary et al., *Nature*, 339:394 (1989), Brinkmann et al., *Proc. Nat'l Acad. Sci. USA*, 88:8616 (1991), Batra et al., *Proc. Nat'l Acad. Sci. USA*, 89:5867 (1992), Friedman et al., *J. Immunol.*, 150:3054 (1993), Wels et al., *Int. J. Can.*, 60:137 (1995), Fominaya et al., *J. Biol. Chem.*, 271:10560 (1996), Kuan et al., *Biochemistry*, 35:2872 (1996) and Schmidt et al., *Int. J. Can.*, 65:538 (1996). Antibody-toxin fusion proteins containing a diphtheria toxin moiety have been described by Kreitman et al., *Leukemia*, 7:553 (1993), Nicholls et al., *J. Biol. Chem.*, 268:5302 (1993), Thompson et al., *J. Biol. Chem.*, 270: 28037 (1995) and Vallera et al., *Blood*, 88:2342 (1996). Deonarain et al. (*Tumor Targeting*, 1:177 (1995)) have described an antibody-toxin fusion protein having an RNase moiety, while Linardou et al. (*Cell Biophys.*, 24-25:243 (1994)) produced an antibody-toxin fusion protein comprising a DNase I component. Gelonin was used as the toxin moiety in the antibody-toxin fusion protein of Wang et al. See Abstracts of the 209th ACS National Meeting, Anaheim, Calif., 2-6 Apr. 1995, Part 1, BIOT005. As a further example, Dohlsten et al. (*Proc. Nat'l Acad. Sci. USA*, 91:8945 (1994)) reported an antibody-toxin fusion protein comprising *Staphylococcal* enterotoxin-A.

Useful cancer chemotherapeutic drugs for the preparation of immunoconjugates include calicheamicin, nitrogen mustards, alkyl sulfonates, nitrosoureas, triazenes, folic acid analogs, pyrimidine analogs, purine analogs, antibiotics, epipodophyllotoxins, platinum coordination complexes, hormones, and the like. Suitable chemotherapeutic agents are described in REMINGTON'S PHARMACEUTICAL SCIENCES (Mack Publishing Co. 1995) and in GOODMAN AND GILMAN'S THE PHARMACOLOGICAL BASIS OF THERAPEUTICS (MacMillan Publishing Co. 1985). Other suitable chemotherapeutic agents, such as experimental drugs, are known to those of skill in the art.

In addition, therapeutically useful immunoconjugates can be obtained by conjugating photoactive agents or dyes to an antibody composite. Fluorescent and other chromogens or dyes, such as porphyrins sensitive to visible light, have been used to detect and to treat lesions by directing the suitable light to the lesion. In therapy, this has been termed photoradiation, phototherapy, or photodynamic therapy. See Jori et al. (eds.), PHOTODYNAMIC THERAPY OF TUMORS AND OTHER DISEASES (Libreria Progetto 1985); van den Bergh, *Chem. Britain*, 22:430 (1986). Moreover, monoclonal antibodies have been coupled with photoactivated dyes for achieving phototherapy. See Mew et al., *J. Immunol.*, 130:1473 (1983); Mew et al., *Cancer Res.*, 45:4380 (1985); Oseroff et al., *Proc. Natl. Acad. Sci. USA*, 83:8744 (1986); Mew et al., *Photochem. Photobiol.*, 46:83 (1987); Hasan et al., *Prog. Clin. Biol. Res.*, 288:471 (1989); Tatsuta et al., *Lasers Surg. Med.*, 9:422 (1989); Pelegrin et al., *Cancer*, 67:2529 (1991). However, these earlier studies did not include use of endoscopic therapy applications, especially with the use of antibody fragments or subfragments. Thus, the present invention contemplates the therapeutic use of immunoconjugates comprising photoactive agents or dyes.

Multimodal therapies of the present invention further include immunotherapy comprising two or more naked anti-granulocyte antibodies. In another embodiment, multimodal therapy comprises administration of naked anti-granulocyte antibodies supplemented with naked antibodies directed to antigens present on a single granulocyte precursor. For example, naked MN-3 antibodies can be administered in conjunction with anti-CD33 and/or anti-CD15 antibodies.

In another embodiment of the present invention, naked antibodies are administered to a patient in combination with an inducing agent, wherein the inducing agent induces or enhances the expression of a targeted antigen in cell-type of interest. A variety of inducing agents are well-known in the art. For example, arsenic oxide has been shown to up-regulate the expression of NCA-90 in acute promyelocytic leukemia cells. See Di Noto et al., *Tissue Antigens*, 54:597-602 (1999). Similarly, retinoic acid also enhances the expresson of NCA-90 in acute promyelocytic leukemia cells. See Boccuni et al., *Tissue Antigens*, 52:1-8 (1998).

By up-regulating the expression of the target antigen on the cell surface, such inducing agents enhance the efficacy the administered immunotherapy. Thus, in one embodiment, inducing agents are co-administered with the naked antibodies of the present invention to enhance the toxicity of the therapy.

In another embodiment, inducing agents are co-administered with naked antibodies to increase the therapeutic scope of the treatment. By inducing expression of antigens not normally displayed on surface of particular cell-types, inducing agents extend the. therapeutic potential of the therapy to additional cell-types and cancers. For example, retinoic acid or arsenic oxide can be administered to up-regulate NCA-90 in acute promyelocytic leukemia cells. See Di Noto et al., *Tissue Antigens*, 54:597-602(1999); Boccuni et al., *Tissue Antigens*, 52:1-8 (1998). Accordingly, the antibodies of the present invention can be used to treat AML, as well as CML.

In another form of multimodal therapy, subjects receive naked anti-granulocyte antibodies and standard chemotherapy. Examples of chemotherapeutic agents include, but are not limited to, daunorubicin, cytarabine, 6-thioguanine, etoposide, mitoxantrone, diaziquone, idarubicin, homoharringtonine, Amsacrine, busulfan, hydroxyurea, calicheamicin, CVB (1.5 g/m$^2$ cyclophosphamide, 200-400 mg/m$^2$ etoposide, and 150-200 mg/m$^2$ carmustine), C-MOPP (cyclophosphamide, vincristine, procarbazine and prednisone), CHOP (cyclophosphamide, doxorubicin, vincristine, and prednisone), m-BACOD (methotrexate, bleomycin, doxorubicin, cyclophosphamide, vincristine, dexamethasone and leucovorin) and MACOP-B (methotrexate, doxorubicin, cyclophosphamide, vincristine, prednisone, bleomycin and leucovorin). Additional useful drugs include phenyl butyrate and bryostatin-1.

In general, the dosage of administered naked anti-granulocyte antibodies, immunoconjugates, fusion proteins and additional therapeutics will vary depending upon such factors as the patient's age, weight, height, sex, general medical condition, disease state and previous medical history. Typically, it is desirable to provide the recipient with a dosage of antibody, immunoconjugate or fusion protein which is in the range of from about 1 pg/kg to 20 mg/kg (amount of agent/body weight of patient), although a lower or higher dosage also may be administered as circumstances dictate.

Administration of antibodies, antibody components, immunoconjugates or fusion proteins to a patient can be intravenous, intraarterial, intraperitoneal, intramuscular, subcutaneous, intrapleural, intrathecal, by perfusion through a regional catheter or by direct intralesional injection. When administering therapeutic proteins by injection, the administration may be by continuous infusion or by single or multiple boluses.

Those of ordinary skill in the art are aware that intravenous injection provides a useful mode of administration due to the thoroughness of the circulation in rapidly distributing antibodies. Intravenous administration, however, is subject to limitation by a vascular barrier comprising endothelial cells of the vasculature and the subendothelial matrix. Still, the vascular barrier is a more notable problem for the uptake of therapeutic antibodies by solid tumors. Lymphomas have relatively high blood flow rates, contributing to effective antibody delivery. Intralymphatic routes of administration, such as subcutaneous or intramuscular injection, or by catherization of lymphatic vessels, also provide a useful means of treating lymphomas.

Preferably, naked anti-granulocyte antibodies are administered at low protein doses, such as 20 to 1500 milligrams protein per dose, given once, or repeatedly, parenterally. Alternatively, naked anti-granulocyte antibodies are administered in doses of 20 to 1000 milligrams protein per dose, or 20 to 500 milligrams protein per dose, or 20 to 100 milligrams protein per dose.

As described above, the present invention also contemplates therapeutic methods in which naked anti-granulocyte antibody components are supplemented with immunoconjugate or fusion protein administration. In one variation, naked anti-granulocyte antibodies are administered with low-dose radiolabeled anti-granulocyte antibodies or fragments. As a second alternative, naked anti-granulocyte antibodies are administered with low-dose radiolabeled anti-granulocyte-cytokine immunoconjugates. As a third alternative, naked anti-granulocyte antibodies are administered with anti-granulocyte-cytokine immunoconjugates that are not radiolabeled. With regard to "low doses" of $^{131}$I-labeled immunoconjugates, a preferable dosage is in the range of 15 to 40 mCi, while the most preferable range is 20 to 30 mCi. In contrast, a preferred dosage of $^{90}$Y-labeled immunoconjugates is in the range from 10 to 30 mCi, while the most preferable range is 10 to 20 mCi.

Immunoconjugates having a boron addend-loaded carrier for thermal neutron activation therapy will normally be effected in similar ways. However, it will be advantageous to wait until non-targeted immunoconjugate clears before neutron irradiation is performed. Clearance can be accelerated using an antibody that binds to the immunoconjugate. See U.S. Pat. No. 4,624,846, which is hereby incorporated by reference in its entirety.

The anti-granulocyte antibodies, immunoconjugates, and fusion proteins of the present invention can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known in the art. See REMINGTON'S PHARMACEUTICAL SCIENCES (Mack Publishing Co. 1995).

For purposes of therapy, the antibodies described in the invention and a pharmaceutically acceptable carrier are administered to a patient in a therapeutically effective amount. A combination of an antibody, optionally with an immunoconjugate/fusion protein, and a pharmaceutically acceptable carrier is said to be administered in a "therapeutically effective amount" if the amount administered is physiologically significant. An agent is physiologically significant if its presence results in a detectable change in the physiology of a recipient patient. In the present context, an agent is physiologically significant if its presence results in the inhibition of the growth of target tumor cells.

Additional pharmaceutical methods can be employed to control the duration of action of an antibody, immunoconjugate or fusion protein in a therapeutic application. Controlled release preparations can be prepared through the use of polymers to complex or adsorb the antibody, immunoconjugate or fusion protein. For example, biocompatible polymers include matrices of poly(ethylene-co-vinyl acetate) and matrices of a polyanhydride copolymer of a stearic acid dimer and sebacic acid. See Sherwood et al., *BioTechnology*, 10:1446 (1992). The rate of release of an antibody (or immunoconjugate) from such a matrix depends upon the molecular weight of the protein, the amount of antibody/immunoconjugate/fusion protein within the matrix, and the size of dispersed particles. See Saltzman et al., *Biophys. J.*, 55:163 (1989); Sherwood et al., *BioTechnology*, 10:1446 (1992). Other solid dosage forms are described in REMINGTON'S PHARMACEUTICAL SCIENCES (Mack Publishing Co. 1995).

The present invention also contemplates a method of treatment in which immunomodulators are administered to prevent, mitigate or reverse radiation-induced or drug-induced toxicity of normal cells, and especially hematopoietic cells. Adjunct immunomodulator therapy allows the administration of higher doses of cytotoxic agents due to increased tolerance of the recipient mammal. Moreover, adjunct immunomodulator therapy can prevent, palliate or reverse dose-limiting marrow toxicity. Examples of suitable immunomodulators for adjunct therapy include G-CSF, GM-CSF, thrombopoietin, IL-1, IL-3, IL-12 and the like. The method of adjunct immunomodulator therapy is disclosed by Goldenberg, U.S. Pat. No. 5,120,525, which is hereby incorporated by reference in its entirety.

For example, recombinant IL-2 may be administered intravenously as a bolus at $6 \times 10^5$ IU/kg or as a continuous infusion at a dose of $18 \times 10^6$ IU/m$^2$/d. See Weiss et al., *J. Clin. Oncol.*, 10:275 (1992). Alternatively, recombinant IL-2 may be administered subcutaneously at a dose of $12 \times 10^6$ IU. Vogelzang et al., *J. Clin. Oncol.*, 11:1809 (1993). INF-γ can be administered subcutaneously at a dose of $1.5 \times 10^6$ U. See Lienard et al., *J. Clin. Oncol.*, 10:52 (1992). Nadeau et al. (*J. Pharmacol. Exp. Ther.*, 274:78 (1995)) have shown that a single intravenous dose of recombinant IL-12 (42.5 µg/kilogram) elevated IFN-γ levels in rhesus monkeys. Suitable IL-2 formulations include PROLEUKIN (Chiron Corp., Emeryville, Calif.) and TECELEUKIN (Hoffmann-La Roche, Inc.; Nutley, N.J.). ACTIMMUNE (Genentech, Inc., South San Francisco, Calif.) is a suitable INF-γ preparation.

The following examples are provided by way of illustration and are not intended to be limiting of the present invention.

EXAMPLES

1. Method of Treating CML Using Naked Anti-NCA-90 Antibody

A patient with CML is treated with IFN-alpha2b for six months, but demonstrates a slow progression into the accelerated phase, with marked increase in Ph1 cells in the marrow. At this time, the patient is infused with 500 mg of naked, humanized MN-3 monoclonal antibody each week, for a total of four weeks. After six weeks the Ph1 cells in the marrow are reduced to very low numbers, and after 10 weeks are undetectable. A year later, the patient demonstrates rapid progression, as evidenced by increases in Ph1 cells, anemia and thrombocytopenia. The four week hMN3 therapy is repeated. Two months after therapy, Ph1 cells are not detected in the marrow, and both red cells and platelets are at normal levels.

2. Method of Treating CML Using Combination Therapy Comprising Naked Anti-NCA-90 Antibody A patient with CML is treated with IFN-alpha2b for six months, but demonstrates a slow progression into the accelerated phase, with marked increase in Ph1 cells in the marrow. At this time, the patient is infused with 500 mg of naked, humanized MN-3 monoclonal antibody each week, for a total of four weeks. After six weeks, the Ph1 cells in the marrow are reduced to very low numbers, and after 10 weeks they are undetectable. A year later, the patient demonstrates rapid progression, as evidenced by increases in Ph1 cells, anemia and thrombo-cytopenia. The four week, hMN3 therapy is repeated, but combined with naked immunotherapy comprising humanized, anti-CD33 antibody, administered at a similar dose. Two months after combination therapy, Ph1 cells are not detectable in the marrow, and both red cells and platelets are at normal levels.

3. Method of Treating APML Using Naked Anti-NCA-90 Antibody

Retinoic acid therapy is initiated in a patient diagnosed with acute promyelocytic leukemia. When NCA-90 is found to have been induced on the malignant cells, the patient is given an infusion of 500 mg of humanized MN-3. The therapy is repeated each week for a total of four infusions. Bone marrow examination after MN-3 therapy demonstrates that the malignant cells undergo apoptosis. Three months later, normal cells predominate in the patient's marrow.

It will occur to those of ordinary skill in the art that various modifications may be made to the disclosed embodiments and that such modifications are intended to be within the scope of the present invention, which is defined by the following claims.

We claim:

1. A method for treating acute promyelocytic leukemia (APML) in a patient, comprising administering to said patient a therapeutic composition comprising a pharmaceutically acceptable carrier and at least one naked anti-NCA-90 granulocyte antibody; and arsenic oxide or retinoic acid, wherein said arsenic oxide or retinoic acid induces expression of NCA-90 which is minimally displayed on the surface of myeloblasts.

2. The method of claim 1, wherein the composition comprises arsenic oxide.

3. A method for treating acute promyelocytic leukemia (APML) in a patient, comprising administering to said patient a therapeutic composition comprising a pharmaceutically acceptable carrier and at least one naked anti-NCA-90 granulocyte antibody, wherein said antibody is MN-3, MN-15, NP-1, or a humanized version thereof; and arsenic oxide or retinoic acid, wherein said arsenic oxide or retinoic acid induces expression of NCA-90 which is minimally displayed on the surface of myeloblasts.

4. The method of claim 1, wherein the composition comprises retinoic acid.

5. A method for treating acute promyelocytic leukemia (APML) in a patient, comprising:

administering to said patient a therapeutic composition comprising a pharmaceutically acceptable carrier;

at least one humanized naked anti-NCA-90 granulocyte antibody, wherein the antibody is a humanized version of MN-3, MN-15 or NP-1; and arsenic oxide or retinoic acid, wherein said arsenic oxide or retinoic acid induces expression of NCA-90 which is minimally displayed on the surface of myeloblasts.

6. The method of claim 5, wherein the composition comprises retinoic acid.

* * * * *